US012782345B2

(12) United States Patent
Xu et al.

(10) Patent No.: US 12,782,345 B2
(45) Date of Patent: Nov. 3, 2026

(54) ADDITIVE, SURFACE TREATMENT AGENT, SURFACE-MODIFIED LATEX PARTICLES, METHOD FOR PRODUCING SURFACE-MODIFIED LATEX PARTICLES, REAGENT FOR LATEX AGGLUTINATION REACTION, KIT, AND METHOD FOR DETECTING TARGET SUBSTANCE

(71) Applicants: Medical & Biological Laboratories Co., Ltd., Tokyo (JP); MBL Materials Co., Ltd., Tsukuba (JP)

(72) Inventors: Yingjia Xu, Minato-ku (JP); Masaaki Miyaji, Manato-ku (JP); Kouji Tamori, Minato-ku (JP); Tokio Sawai, Minato-ku (JP); Hiroyuki Honma, Minato-ku (JP); Naoki Hayashi, Minato-ku (JP); Shin-Ya Omote, Minato-ku (JP)

(73) Assignees: Medical & Biological Laboratories Co., Ltd., Tokyo (JP); MBL Materials Co., Ltd. Medical & Biological Laboratories Co., Ltd., Ibaraki (JP)

( * ) Notice: Subject to any disclaimer, the term of this patent is extended or adjusted under 35 U.S.C. 154(b) by 99 days.

(21) Appl. No.: 17/817,684

(22) Filed: Aug. 5, 2022

(65) Prior Publication Data

US 2022/0380503 A1 Dec. 1, 2022

Related U.S. Application Data

(62) Division of application No. 16/076,070, filed as application No. PCT/JP2017/004730 on Feb. 9, 2017, now Pat. No. 11,493,506.

(30) Foreign Application Priority Data

Feb. 12, 2016 (JP) ................................ 2016-025316

(51) Int. Cl.
*C08F 220/56* (2006.01)
*G01N 33/543* (2006.01)

(52) U.S. Cl.
CPC ..... *G01N 33/54313* (2013.01); *C08F 220/56* (2013.01); *G01N 33/54393* (2013.01)

(58) Field of Classification Search
CPC ........ G01N 33/54313; G01N 33/54393; C08F 220/56
See application file for complete search history.

(56) References Cited

U.S. PATENT DOCUMENTS

| | | | |
|---|---|---|---|
| 10,640,732 B2 * | 5/2020 | Iso ....................... | C11D 3/3765 |
| 2004/0157276 A1 | 8/2004 | Sumida et al. | |
| 2009/0124707 A1 | 5/2009 | Tamori et al. | |
| 2012/0070912 A1 | 3/2012 | Kitsugi | |

FOREIGN PATENT DOCUMENTS

| | | | |
|---|---|---|---|
| JP | 7-83923 A | | 3/1995 |
| JP | 8-110340 A | | 4/1996 |
| JP | 8-278308 A | | 10/1996 |
| JP | 11-287802 A | | 10/1999 |
| JP | 2002-365296 A | | 12/2002 |
| JP | 2003-294753 A | | 10/2003 |
| JP | 2006-105910 A | | 4/2006 |
| JP | 2006-266970 A | | 10/2006 |
| JP | 2009-133809 A | | 6/2009 |
| JP | 2014153140 A | * | 8/2014 |
| WO | WO-2015119256 A1 | * | 8/2015 |

OTHER PUBLICATIONS

Ele et al. ("Synthesis of 4-Acryloylmorpholine-based Hydrogels and Investigation of their Drug Release Behaviors", J. Braz. Chem. Soc., vol. 24, No. 5, pp. 814-820, published 2013) (Year: 2013).*
Peppas et al. ("Hydrogels in pharmaceutical formulations", European Journal of Pharmaceutics and Biopharmaceutics 50 (2000), pp. 27-46). (Year: 2000).*
Mukherjee et al. ("Self-healing hydrogels containing reversible oxime crosslinks", Soft Matter, 2015, vol. 11, pp. 6152-6161). (Year: 2015).*
International Search Report issued Apr. 25, 2017 in PCT/JP2017/004730 filed Feb. 9, 2017.
Extended European Search Report issued Jun. 13, 2019 in corresponding European Patent Application No. 17750329.9, 7 pages.
Japanese Office Action issued Nov. 10, 2020 in Japanese Patent Application No. 2017-566998 (with unedited computer generated English translation), 6 pages.

* cited by examiner

*Primary Examiner* — Shafiqul Haq
*Assistant Examiner* — Nam P Nguyen
(74) *Attorney, Agent, or Firm* — Oblon, McClelland, Maier & Neustadt, L.L.P.

(57) ABSTRACT

Provided are an additive and a surface treatment agent capable of suppressing agglutination of latex particles contained in a reagent for a latex agglutination reaction during storage of the reagent although a synthetic polymer is contained as an active component.

An additive is to be added to latex particles used in a reagent for a latex agglutination reaction. The latex particles have not been subjected to blocking treatment. The additive includes a polymer containing more than 60% by mass and 99% by mass or less of hydrophilic repeating units (A) relative to all repeating units and 1% by mass or more and less than 40% by mass of hydrophobic repeating units (B) relative to all repeating units, and having a weight average molecular weight of 3,000 or more.

7 Claims, 1 Drawing Sheet

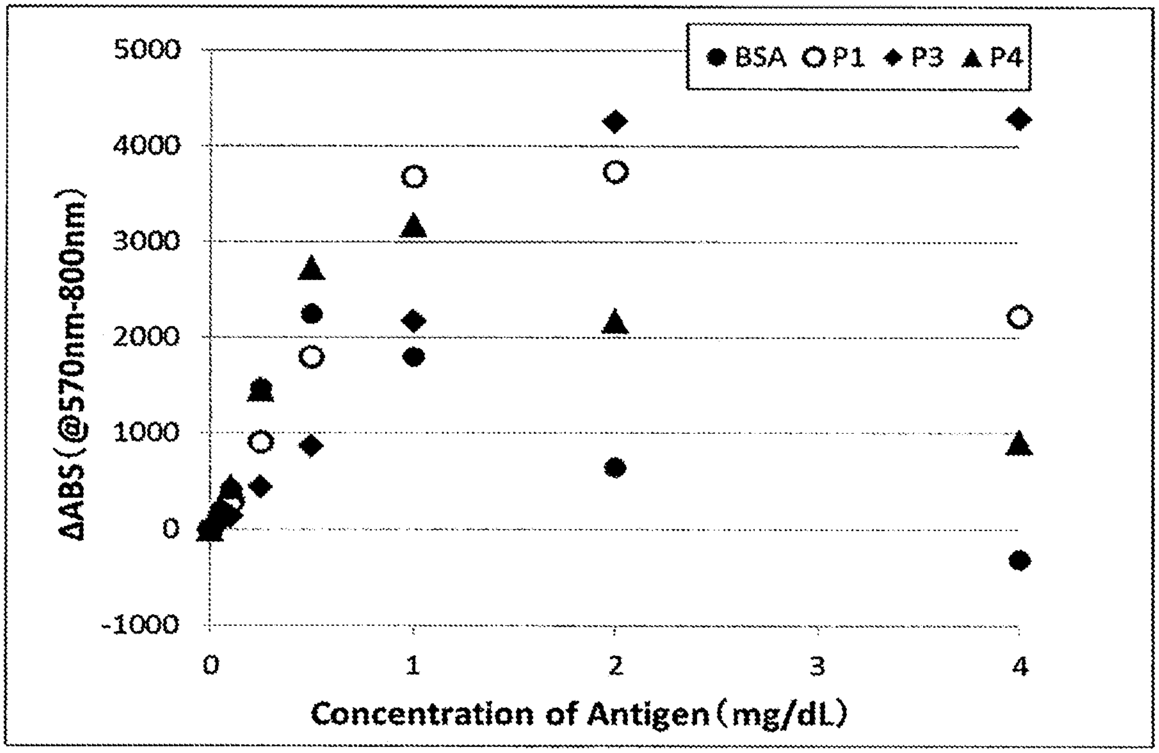
● BSA ○ P1 ◆ P3 ▲ P4
5000
4000
3000
2000
1000
0
-1000
ΔABS(@570nm-800nm)
0
1
2
3
4
Concentration of Antigen(mg/dL)

ADDITIVE, SURFACE TREATMENT AGENT, SURFACE-MODIFIED LATEX PARTICLES, METHOD FOR PRODUCING SURFACE-MODIFIED LATEX PARTICLES, REAGENT FOR LATEX AGGLUTINATION REACTION, KIT, AND METHOD FOR DETECTING TARGET SUBSTANCE

The present application is a divisional of U.S. application Ser. No. 16/076,070, filed Aug. 7, 2018, which is the National Stage of International Application no. PCT/JP2017/004730, filed Feb. 9, 2017, which claims priority to Japanese Patent Application No. 2016-025316, filed Feb. 12, 2016. The contents of these applications are incorporated herein by reference in their entireties.

TECHNICAL FIELD

The present invention relates to an additive, a surface treatment agent, surface-modified latex particles, a method for producing surface-modified latex particles, a reagent for a latex agglutination reaction, a kit, and a method for detecting a target substance.

BACKGROUND ART

A latex agglutination method using an agglutination reaction occurring between a target substance such as an antigen (antibody) and an antibody (antigen) against the target substance is widely utilized in regions, for example, of a clinical test and biochemical studies (Patent Literature 1). This latex agglutination method is performed, for example, by mixing a specimen that may contain a target substance with a first reagent such as a buffer and mixing this mixed solution with a reagent for a latex agglutination reaction (second reagent) containing latex particles to which an antibody (antigen) against the target substance is immobilized. In a case where the target substance is present in the specimen, an agglutination reaction of the latex particles occurring as a result of an antigen-antibody reaction is detected.

However, in the latex agglutination method, insufficient detection sensitivity may be pointed out in a case where latex particles having small particle sizes are used, for example.

Therefore, a sensitizer that promotes a latex agglutination reaction has been proposed. As such a sensitizer, a water-soluble polymer such as polyethylene glycol, a polyhydric alcohol, polyvinyl pyrrolidone, carboxymethyl cellulose, dextran, alginic acid, an aminoethanesulfonic acid derivative, or an aminopropanesulfonic acid derivative is known (Patent Literatures 2 to 4) Detection sensitivity is enhanced by adding the water-soluble polymer to a reagent and keeping the resulting mixture under certain conditions.

However, the above water-soluble polymer causes agglutination of latex particles due to a factor other than an antigen-antibody reaction (for example, nonspecific adsorption) disadvantageously. There are problems, for example, noise is generated by this agglutination, and latex particles in a reagent for a latex agglutination reaction agglutinate in a case where the water-soluble polymer is blended with the reagent and stored.

CITATION LIST

Patent Literature

Patent Literature 1: JP-A 2006-266970
Patent Literature 2: JP-A H8-278308

Patent Literature 3: JP-A 2003-294753
Patent Literature 4: JP-A 2006-105910

SUMMARY OF INVENTION

Technical Problem

Under the above background, in order to suppress (block) agglutination due to a factor other than an antigen-antibody reaction, a biological substance such as albumin, casein, gelatin, or skim milk is treated on surfaces of latex particles as a surface treatment agent.

However, in a case where the above biological substance is used as a surface treatment agent, a problem such as bio-contamination typified by BSE or a difference between lots of products is concerned.

The present invention is to provide an additive and a surface treatment agent capable of suppressing agglutination of latex particles contained in a reagent for a latex agglutination reaction during storage of the reagent although a synthetic polymer is contained as an active component.

Solution to Problem

Thus, the inventors of the present invention conducted a thorough investigation. As a result, the present inventors found that by adding a polymer having a specific amount of hydrophilic repeating units and a specific amount of hydrophobic repeating units and having a specific weight average molecular weight to latex particles that have not been subjected to blocking treatment, that is, by treating surface of the latex particles with the polymer, agglutination of latex particles is suppressed.

That is, the present invention provides the following [1] to [18].

[1] An additive (hereinafter also referred to as the additive of the present invention) to be added to latex particles used in a reagent for a latex agglutination reaction, in which the latex particles have not been subjected to blocking treatment, and the additive includes a polymer (hereinafter also referred to as a specific polymer) containing more than 60% by mass and 99% by mass or less of hydrophilic repeating units (A) (hereinafter also referred to simply as repeating units (A)) relative to all repeating units and 1% by mass or more and less than 40% by mass of hydrophobic repeating units (B) (hereinafter also referred to simply as repeating units (B)) relative to all repeating units, and having a weight average molecular weight of 3,000 or more.

[2] A surface treatment agent (hereinafter also referred to as the surface treatment agent of the present invention) to be used for surface treatment of latex particles used in a reagent for a latex agglutination reaction, containing a specific polymer.

[3] The agent according to [1] or [2], containing one or more selected from the group consisting of a polyalkylene glycol chain, a zwitterionic structure, a heterocyclic group, an ester bond, an amide bond, a hydroxy group, an epoxy group, an isocyanate group, a blocked isocyanate group, a carboxylic acid anhydride group, and an amino group in the repeating unit (A).

[4] The agent according to any one of [1] to [3], containing one or more selected from the group consisting of a polyalkylene glycol chain, a zwitterionic structure, a heterocyclic group, an ester bond, and an amide bond in the repeating unit (A).

[5] The agent according to any one of [1] to [4], containing one or more selected from the group consisting of a hydrophilic repeating unit derived from a (meth)acrylamide-based monomer and a hydrophilic repeating unit derived from a (meth)acrylate-based monomer, as the repeating unit (A).

[6] The agent according to [5], in which the hydrophilic repeating unit derived from the (meth)acrylate-based monomer has a polyalkylene glycol chain or a zwitterionic structure in a side chain thereof.

[7] The agent according to any one of [1] to [6], containing one or more selected from the group consisting of a keto group, an ester bond, an amide bond, and an aromatic hydrocarbon group in the repeating unit (B).

[8] The agent according to any one of [1] to [7], containing one or more selected from the group consisting of a hydrophobic repeating unit derived from a (meth)acrylamide-based monomer, a hydrophobic repeating unit derived from a (meth)acrylate-based monomer, and a hydrophobic repeating unit derived from a styrene-based monomer, as the repeating unit (B).

[9] The agent according to any one of [1] to [6], containing one or more selected from the group consisting of a hydrophobic repeating unit represented by t following formula (7) and a hydrophobic repeating unit represented by the following formula (8), as the repeating unit (B).

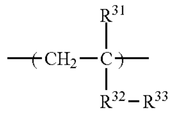

(7)

[In formula (7), $R^{31}$ represents a hydrogen atom or a methyl group, $R^{32}$ represents —O—, *—(C═O)—O—, *—(C═O)—$NR^{34}$—, *—$NR^{34}$—(C═O)—($R^{34}$ represents a hydrogen atom or an organic group having 1 to 10 carbon atoms, and * represents a position bonded to a carbon atom to which $R^{31}$ in formula (7) is bonded), or a phenylene group, and $R^{33}$ represents a hydrocarbon group.]

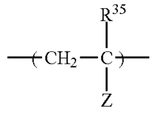

(8)

[In formula (8), $R^{35}$ represents a hydrogen atom or a methyl group, and

Z represents an organic group having a formyl group or a keto group.]

[10] The agent according to any one of [1] to [9], in which the polymer has a weight average molecular weight of 3,000 to 1,000,000.

[11] The agent according to any one of [1] to [10], in which the polymer is water-soluble.

[12] The agent according to any one of [1] to [11], in which the latex particles have a ligand for a target substance immobilized thereto.

[13] Surface-modified latex particles (hereinafter also referred to as the surface-modified latex particles of the present invention) having a specific polymer on surfaces thereof.

[14] A method for producing surface-modified latex particles (hereinafter also referred to as the method for producing surface-modified latex particles according to the present invention), including a contact step of bringing a specific polymer into contact with latex particles.

[15] Surface-modified latex particles obtained by the production method according to [14].

[16] A reagent for a latex agglutination reaction (hereinafter also referred to as the reagent for a latex agglutination reaction of the present invention), containing the surface-modified latex particles according to [13] or [15].

[17] A kit (hereinafter also referred to as the kit of the present invention) to be used for detecting a target substance in a specimen by a latex agglutination method, including the reagent for latex agglutination reaction according to [16].

[18] A method for detecting a target substance (hereinafter also referred to as the method for detecting a target substance according to the present invention), including: a mixing step of mixing the reagent for a latex agglutination reaction according to [16] with a specimen; and a detection step of optically detecting an agglutination reaction generated in the mixing step.

Advantageous Effects of Invention

By adding the additive of the present invention to latex particles that have not been subjected to blocking treatment, agglutination of the latex particles can be suppressed in a case where the latex particles are stored while being contained in a reagent for a latex agglutination reaction.

By subjecting the latex particles to the surface treatment with the surface treatment agent of the present invention, agglutination of the latex particles can be suppressed in a case where the latex particles are stored while being contained in a reagent for a latex agglutination reaction.

The surface-modified latex particles of the present invention hardly agglutinate even in a case of being stored in a reagent for a latex agglutination reaction.

BRIEF DESCRIPTION OF DRAWINGS

FIG. 1 is a graph illustrating a prozone suppression effect in a case where latex particles are surface-treated using copolymers (P1), (P3), and (P4).

DESCRIPTION OF EMBODIMENTS

<Additive and Surface Treatment Agent>

The additive of the present invention is to be added to latex particles used in a reagent for a latex agglutination reaction, characterized in that the latex particles have not been subjected to blocking treatment, and the additive includes a polymer containing more than 60% by mass and 99% by mass or less of hydrophilic repeating units (A) relative to all repeating units and 1% by mass or more and less than 40% by mass of hydrophobic repeating units (B) relative to all repeating units, and having a weight average molecular weight of 3,000 or more.

The surface treatment agent of the present invention is to be used for surface treatment of latex particles used in a reagent for a latex agglutination reaction, characterized by including a polymer containing more than 60% by mass and 99% by mass or less of hydrophilic repeating units (A) relative to all repeating units and 1% by mass or more and less than 40% by mass of hydrophobic repeating units (B) relative to all repeating units, and having a weight average molecular weight of 3,000 or more.

Here, the term “latex particles that have not been subjected to blocking treatment” referred to herein means latex particles that have not been subjected to blocking treatment (surface treatment) using, for example, a biological substance such as albumin, casein, gelatin, or skim milk, or a synthetic polymer such as a blocking reagent N101 (NOF CORPORATION), a blocking reagent N102 (NOF CORPORATION), Lipidure (registered trademark)-BL 103, Lipidure-BL 203, or Lipidure-BL 802 (NOF CORPORATION).

The term "surface treatment" referred to herein means bringing a specific polymer into direct contact latex particles such that the specific polymer adheres to a part or the whole of surfaces of the latex particles.

Incidentally, each of the additive and the surface treatment agent of the present invention may contain only one kind or two or more kinds among polymers corresponding to the specific polymer. The phrase "A to B" representing a numerical range or the like referred to herein means A or more and B or less, and A and B are included in the numerical range.

Next, the specific polymer will be described.

The specific polymer has a hydrophilic repeating unit (A). This makes it easier to suppress nonspecific adsorption to latex particles when an additive and a surface treatment agent are used.

In addition, the specific polymer has more than 60% by mass and 99% by mass or less of hydrophilic repeating units (A) relative to all repeating units. If the content of the repeating unit (A) is 60% by mass or less, agglutination tends to occur during storage of the reagent for a latex agglutination reaction. If the content of the repeating unit (A) exceeds 99% by mass, the specific polymer does not sufficiently adhere to the latex particles, and agglutination tends to occur during storage of the reagent for a latex agglutination reaction similarly to the above case.

The term "hydrophilic" means having a strong affinity with water. Specifically, in a case where a homopolymer containing only one kind of repeating unit (having a number average molecular weight of about 10,000 according to a measuring method in Examples) is used, if 1 g or more of the homopolymer is dissolved in 100 g of pure water at room temperature (25° C.), the repeating unit is hydrophilic.

The content of the repeating unit (A) is preferably 65% by mass or more, more preferably 70% by mass or more, and particularly preferably 75% by mass or more relative to all repeating units from a viewpoint of suppressing agglutination during storage of the reagent for a latex agglutination reaction. The content of the repeating unit (A) is preferably 97.5% by mass or less, and particularly preferably 95% by mass or less relative to all repeating units from a viewpoint of making it difficult for a specific polymer to peel off from surfaces of the particles after the specific polymer adheres to the particles.

In particular, by setting the content of the repeating unit (A) to 75% by mass or more, even in a case where the reagent for a latex agglutination reaction is stored under a high temperature condition for a long period of time, the latex particles hardly agglutinate.

Note that the content of each repeating unit can be measured by $^{13}$C-NMR, for example.

The zwitterionic structure preferably includes a quaternary ammonium salt type cationic functional group and a monovalent or divalent anionic functional group selected from the group consisting of $—(C{=}O)O^-$, $—SO_3^-$, and $—O—(O{=}P—O^-)—O—$.

The polyalkylene glycol chain is preferably represented by $—(R^1O)n-$ ($R^1$ represents an alkanediyl group having 2 to 4 carbon atoms, and n represents 2 to 100 as an average value).

The number of carbon atoms of the alkanediyl group represented by $R^1$ is preferably 2 or 3, and more preferably 2.

The alkanediyl group represented by $R^1$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Among these groups, an ethane-1,2-diyl group is preferable from viewpoints, for example, of a desired effect of the present invention and availability. Note that n $R^1$s may be the same as or different from one another.

n represents 2 to 100 as an average value, preferably 4 to 90 as an average value, more preferably 8 to 90 as an average value, still more preferably 8 to 60 as an average value, further still more preferably 8 to 40 as an average value, and particularly preferably 9 to 25 as an average value.

Note that each "average value" referred to herein can be measured by NMR. For example, for the structure of the following formula (2), by measuring $^1$H-NMR and comparing integral values of proton peaks of an alkanediyl group represented by $R^1$ and a methyl group at a terminal of an alkyl group represented by $R^2$, it is possible to calculate an average value of n.

Examples of the repeating unit (A) include a repeating unit derived from a monomer having an unsaturated bond at a terminal thereof or a non-terminal thereof. Specific examples of the repeating unit include a repeating unit derived from a (hereinafter also referred to as a (meth) acrylamide-based repeating unit), a repeating unit derived from a (meth)acrylate-based monomer (hereinafter referred to as a (meth)acrylate-based repeating unit), a repeating unit derived from a styrene-based monomer (hereinafter also referred to as a styrene-based repeating unit), and a repeating unit derived from an unsaturated-based monomer. Note Among these units, the repeating unit (A) is preferably a (meth)acrylamide-based repeating unit, a (meth)acrylate-based repeating unit, or a styrene-based repeating unit, and more preferably a (meth)acrylamide-based repeating unit or a (meth)acrylate-based repeating unit. Note that the content of the (meth)acrylate-based repeating unit is preferably 0 to 90% by mass, more preferably 0 to 80% by mass, and particularly preferably 0 to 70% by mass relative to the total amount of the repeating units (A).

Incidentally, as described above, the repeating unit (A) may have, for example, a polyalkylene glycol chain, a zwitterionic structure, or a heterocyclic group such as a morpholino group in a side chain or the like. The repeating unit (A) may have a single kind or two or more kinds among these groups.

Here, among the repeating units (A), a hydrophilic repeating unit (hereinafter also referred to as a repeating unit (A-1)) having a polyalkylene glycol chain in a side chain thereof will be specifically described.

Examples of the repeating unit (A-1) include a repeating unit derived from a similar monomer to the monomer species exemplified as the monomer having an unsaturated bond at a terminal thereof or a non-terminal thereof, and the (repeating unit is particularly preferable.

In the repeating unit (A-1), a hydrogen atom or an alkyl group having 1 to 4 carbon atoms is preferably bonded to a terminal of a polyalkylene glycol chain. Preferable examples of such a repeating unit (A-1) include a hydrophilic repeating unit having a structure represented by the following formula (1) in a side chain thereof. In such a case, a.

$$-(R^1O)_n-R^2 \quad (1)$$

[In formula (1), $R^2$ represents a hydrogen atom or an alkyl group having 1 to 4 carbon atoms, and $R^1$ and n are as defined above.]

(2)

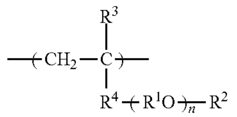

[In formula (2), $R^3$ represents a hydrogen atom or a methyl group, $R^4$ represents —O—, *—(C═O)—O—, *—$NR^5$—(C═O) ($R^5$ represents a hydrogen atom or an organic group having 1 to 10 carbon atoms, and * represents a position bonded to a carbon atom to which $R^3$ in formula (2) is bonded), or a phenylene group, and the other symbols are as defined in formula (1).]

Here, each symbol in formulas (1) and (2) will be described.

$R^2$ represents a hydrogen atom or an alkyl group having 1 to 4 carbon atoms. The number of carbon atoms of the alkyl group represented by $R^2$ is preferably 1 to 3, more preferably 1 or 2, and still more preferably 1 from viewpoints, for example, of a desired effect of the present invention and availability. The alkyl group represented by $R^2$ may be linear or branched, and specific examples thereof include a methyl group, an ethyl group, an n-propyl group, an isopropyl group, an n-butyl group, an isobutyl group, a sec-butyl group, and a tert-butyl group.

Among such $R^2$s, a hydrogen atom and an alkyl group having 1 to 3 carbon atoms are preferable, a hydrogen atom and an alkyl group having 1 or 2 carbon atoms is more preferable, a hydrogen atom and a methyl group are still more preferable, and a methyl group is particularly preferable from viewpoints, for example, of a desired effect of the present invention and availability.

$R^4$ represents —O—, *—(C═O)—O—, *—$NR^5$—(C═O)—, or a phenylene group. Examples of such a phenylene group include a 1,2-phenylene group, a 1,3-phenylene group, and a 1,4-phenylene group.

The number of carbon atoms of the organic group represented by $R^5$ is 1 to 10, and preferably 1 to 6. Examples of the organic group include a hydrocarbon group. Such a hydrocarbon group is a concept including an aliphatic hydrocarbon group, an alicyclic hydrocarbon group, and an aromatic hydrocarbon group.

The aliphatic hydrocarbon group in the $R^5$ may be linear or branched, and specific examples thereof include an alky group such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, or a decyl group.

The alicyclic hydrocarbon group is roughly classified into a monocyclic alicyclic hydrocarbon group and a bridged cyclic hydrocarbon group. Examples of the monocyclic alicyclic hydrocarbon group include a cycloalkyl group such as a cyclopropyl group or a cyclohexyl group. Examples of the bridged cyclic hydrocarbon group include an isobornyl group.

Examples of the aromatic hydrocarbon group include an aryl group such as a phenyl group.

Among the above $R^4$s, *—(C═O)—O— is particularly preferable.

Examples of a monomer constituting the repeating unit (A-1) include polyethylene glycol (meth)acrylate, polypropylene glycol (meth)acrylate, polyethylene glycol polypropylene glycol (meth)acrylate, polyethylene glycol polytetramethylene glycol (meth)acrylate, polypropylene glycol polytetramethylene glycol (meth)acrylate, methoxypolyethyleneglycol (meth)acrylate, and ethoxypolyethyleneglycol (meth)acrylate. These monomers may be used singly or in combination of two or more kinds thereof.

Next, among the repeating units (A), the hydrophilic repeating unit having a zwitterionic structure in a side chain thereof (hereinafter also referred to as a repeating unit (A-2)) will be specifically described.

Examples of the repeating unit (A-2) include a repeating unit derived from a similar monomer to the monomer species exemplified as the monomer having an unsaturated bond at a terminal thereof or a non-terminal thereof, and the (meth)acrylate-based repeating unit is particularly preferable. Specific examples thereof include a hydrophilic repeating unit represented by the following formula (3) or (4). Note that both a hydrophilic repeating unit represented by formula (3) and a hydrophilic repeating unit represented by formula (4) may be contained.

(3)

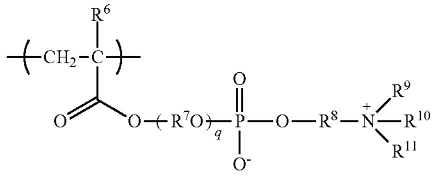

[In formula (3), $R^6$ represents a hydrogen atom or a methyl group, $R^7$ represents an alkanediyl group having 2 to 4 carbon atoms, $R^8$ represents an alkanediyl group having 1 to 10 carbon atoms, $R^9$, $R^{10}$, and $R^{11}$ each independently represent a hydrogen atom or a hydrocarbon group having 1 to 8 carbon atoms, and q represents 1 to 10 as an average value.]

(4)

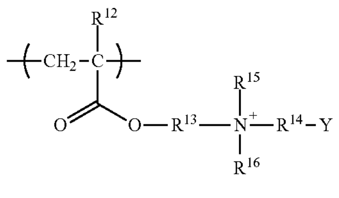

[In formula (4),

Y represents —(C═O)$O^-$, —(O═S═O)$O^-$, —O(O═S═O)$O^-$, —(S═O)$O^-$, —O(S═O)$O^-$, —OP(═O)($OR^{17}$)$O^-$, —OP(═O)$O^-$, —P(═O)(OR')$O^-$, or —P(═O)($R^{17}$)$O^-$ ($R^{17}$ represents an alkyl group having 1 to 3 carbon atoms), $R^{12}$ represents a hydrogen atom or a methyl group, $R^{13}$ and $R^{14}$ each independently represent a divalent organic group having 1 to 10 carbon atoms, and $R^{15}$ and $R^{16}$ each independently represent a hydrocarbon group having 1 to 10 carbon atoms.]

In formula (3), $R^7$ represents an alkanediyl group having 2 to 4 carbon atoms. Incidentally, in a case where there is a plurality of R's, R's may be the same as or different from one another.

The number of carbon atoms of the alkanediyl group represented by $R^7$ is preferably 2 or 3, and more preferably 2.

The alkanediyl group represented by $R^7$ may be linear or branched, and specific examples thereof include an ethane-1,2-diyl group, a propane-1,2-diyl group, a propane-1,3-diyl group, a propane-2,2-diyl group, a butane-1,2-diyl group, a butane-1,3-diyl group, and a butane-1,4-diyl group. Among these groups, an ethane-1,2-diyl group is preferable from viewpoints, for example, of a desired effect of the present invention and availability.

$R^6$ represents an alkanediyl group having 1 to 10 carbon atoms.

The number of carbon atoms of the alkanediyl group represented by $R^8$ is preferably 1 to 6, more preferably 1 to 4, still more preferably 2 or 3, and particularly preferably 2.

The alkanediyl group represented by $R^8$ may be linear or branched, and specific preferable examples thereof include those similar to the alkanediyl group represented by $R^7$.

$R^9$, $R^{10}$, and $R^{11}$ each independently represent a hydrogen atom or a hydrocarbon group having 1 to 8 carbon atoms, and preferably a hydrocarbon group having 1 to S carbon atoms. The number of carbon atoms of such a hydrocarbon group is preferably 1 to 4, more preferably 1 or 2, and particularly preferably 1.

Examples of the hydrocarbon group include an alkyl group; an aryl group such as a phenyl group; and an aralkyl group such as a benzyl group, and an alkyl group is preferable.

The alkyl group may be linear or branched, and specific preferable examples thereof include a methyl group, an ethyl group, an n-propyl group, an isopropyl group, an n-butyl group, an isobutyl group, a sec-butyl group, and a tert-butyl group.

q represents 1 to 10 as an average value, preferably 1 to 7 as an average value, more preferably 1 to 4 as an average value, and still more preferably 1.

Examples of a monomer constituting a repeating unit represented by formula (3) include 2-(meth)acryloyloxyethyl-2'-(trimethylammonio) ethyl phosphate, (2-(meth) acryloyloxyethyl phosphorylcholine), 3-(meth)acryloyloxypropyl-2'-(trimethylammonio) ethyl phosphate, 4-(meth) acryloyloxybutyl-2'-(trimethylammonio) ethyl phosphate, 2-(meth)acryloyloxyethoxyethyl-2'-(trimethylammonio) ethyl phosphate, 2-(meth)acryloyloxydiethoxyethyl-2'-(triethylammonio) ethyl phosphate, 2-(meth)acryloyloxyethyl-2'-(triethylammonio) ethyl phosphate, and 2-(meth)acryloyloxyethyl-2'-(tributylammonio) ethyl phosphate. These monomers may be used singly or in combination of two or more kinds thereof.

In formula (4), Y is preferably —(C═O)$O^-$. Note that examples of the alkyl group represented by $R^{17}$ include a methyl group, an ethyl group, an n-propyl group, and an isopropyl group.

In formula (4), $R^{13}$ and $R^{14}$ each independently represent a divalent organic group having 1 to 10 carbon atoms. The number of carbon atoms of such a divalent organic group is preferably 1 to 8, and more preferably 1 to 6.

The divalent organic group is preferably a divalent hydrocarbon group, and more preferably a divalent aliphatic hydrocarbon group. The divalent aliphatic hydrocarbon group may be linear or branched. The divalent aliphatic hydrocarbon group is preferably an alkanediyl group. Examples of the alkanediyl group include a methane-1,1-diyl group, an ethane-1,2-diyl group, a propane-1,1-diyl group, a propane-1,2-diyl group, a propane-1,3-diyl group, a propane-2,2-diyl group, a butane-1,4-diyl group, a pentane-1,5-diyl group, and a hexane-1,6-diyl group.

In formula (4), $R^{15}$ and $R^{16}$ each independently represent a hydrocarbon group having 1 to 10 carbon atoms. The number of carbon atoms of the hydrocarbon group is preferably 1 to 6, and more preferably 1 to 4.

Examples of the hydrocarbon group represented by $R^{15}$ or $R^{16}$ include an alkyl group; an aryl group such as a phenyl group; and an aralkyl group such as a benzyl group, and an alkyl group is preferable. The alkyl group may be linear or branched, and examples thereof include a methyl group, an ethyl group, an n-propyl group, an isopropyl group, an n-butyl group, an isobutyl group, a sec-butyl group, and a tert-butyl group.

Examples of a monomer constituting a repeating unit represented by formula (4) include N-(meth)acryloyloxyethyl-N,N-dimethylamsnonium-α-N-methylcarboxybetaine and N-(meth)acryloyloxyethyl-N,N-dimethylammonium-α-N-propylsulfobetaine. These monomers may be used singly or in combination of two or more kinds thereof.

Here, the specific polymer preferably contains at least a (meth)acrylamide-based repeating unit as the repeating unit (A). The content of the (meth)acrylamide-based repeating unit is preferably 10 to 100% by mass, more preferably 20 to 100% by mass, and particularly preferably 30 to 100% by mass relative to the total amount of the repeating units (A).

The (meth)acrylamide-based repeating unit may have the or the zwitterionic structure in a side chain thereof, and a hydrophilic repeating unit represented by the following formula (5) or (6) is particularly preferable. Note that both a hydrophilic repeating unit represented by formula (5). The repeating unit (A) preferably contains at least a hydrophilic repeating unit represented by formula (6) from a viewpoint of suppressing agglutination during storage of the reagent for a latex agglutination reaction.

(5)

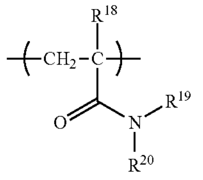

[In formula (5), $R^{18}$ represents a hydrogen atom or a methyl group, and $R^{19}$ and $R^{20}$ each independently represent a hydrogen atom, an alkyl group having 1 to 6 carbon atoms, or a hydroxyalkyl group.]

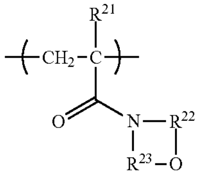

(6)

[In formula (6), $R^{21}$ represents a hydrogen atom or a methyl group, and $R^{22}$ and $R^{23}$ each independently represent an alkanediyl group having 1 to 3 carbon atoms.]

In formula (5), $R^{19}$ and $R^{20}$ each independently represent a hydrogen atom, an alkyl group having 1 to 6 carbon atoms, or a hydroxyalkyl group.

The number of carbon atoms of the alkyl group represented by $R^{19}$ or $R^{20}$ is preferably 1 to 3.

The alkyl group represented by $R^{19}$ or $R^{20}$ may be linear or branched, and specific preferable examples thereof include a methyl group, an ethyl group, an n-propyl group, and an isopropyl group.

The number of carbon atoms of the hydroxyalkyl group represented by $R^{19}$ or $R^{20}$ is preferably 1 to 6, and more preferably 1 to 3. The alkyl group contained in the hydroxyalkyl group may be linear or branched, and specific preferable examples of the hydroxyalkyl group include a hydroxymethyl group, a hydroxyethyl group, a hydroxypropyl group, and a hydroxyisopropyl group. Note that the substitution position of the hydroxy group in the hydroxyalkyl group is arbitrary.

Examples of a monomer constituting a repeating unit represented by formula (5) include dimethyl (meth)acrylamide, diethyl (meth)acrylamide, N-isopropyl (meth)acrylamide, N-(hydroxymethyl) (meth)acrylamide, and N-(2-hydroxyethyl) (meth)acrylamide. These monomers may be used singly or in combination of two or more kinds thereof.

In formula (6), $R^{22}$ and $R^{23}$ each independently represent an alkanediyl group having 1 to 3 carbon atoms. The number of carbon atoms of such an alkanediyl group is preferably 1 or 2.

The alkanediyl group may be linear or branched, but is preferably linear. Specific preferable examples thereof include a methane-1,1-diyl group and an ethane-1,2-diyl group.

Examples of a monomer constituting a repeating unit represented by formula (6) include 4-(meth)acryloyl morpholine.

Note that the specific polymer may contain an anionic repeating unit as the repeating unit (A). Examples of the repeating unit include a repeating unit having an anionic group such as a carboxy group, a sulfo group, or a phosphoric acid group. The repeating unit may contain one or more of these repeating units. The anionic group contained in the repeating unit (A) may form a salt. In this case, examples of the salt include an alkali metal salt such as a sodium salt or a potassium salt; an alkaline earth metal such as a magnesium salt or a calcium salt; an ammonium salt; and an organic ammonium salt.

Examples of a monomer constituting the anionic repeating unit include an unsaturated dicarboxylic acid such as fumaric acid, maleic acid, or itaconic acid or a salt thereof; an unsaturated carboxylic acid such as (meth)acrylic acid or a salt thereof; a sulfo group-containing polymerizable unsaturated monomer such as ethylene sulfonic acid, allyl sulfonic acid, methallylsulfonic acid, 2-sulfoethyl (meth) acrylate, or 2-acrylamido-2-methylpropanesulfonic acid or a salt thereof; a phosphoric acid group-containing polymerizable unsaturated monomer such as 2-(meth)acryloyloxyethyl acid phosphate or 2-(meth)acryloyloxypropyl acid phosphate or a salt thereof. The monomer constituting the anionic repeating unit can also be obtained by using, for example, a hydrolyzate of an acrylate; a hydrolyzate of an acid anhydride of an unsaturated dicarboxylic acid such as maleic anhydride or itaconic anhydride; or an adduct of an acidic group-containing thiol to an epoxy group, such as glycidyl methacrylate or (4-vinylbenzyl) glycidyl ether.

(Repeating Unit (B))

The specific polymer of the present invention has a hydrophobic repeating unit (B). This makes it easier for the specific polymer to adhere to the latex particles when an additive and a surface treatment agent are used.

The term "hydrophobic" means having a weak affinity with water. Specifically, in a case where a homopolymer containing only one kind of repeating unit (having a number average molecular weight of about 10,000 according to a measuring method in Examples) is used, if less than 1 g of the homopolymer is dissolved in 100 g of pure water at room temperature (25° C.), the repeating unit is hydrophobic.

The content of the repeating unit (B) is 1% by mass or more and less than 40% by mass relative to all repeating units. When the content of the repeating unit (B) is less than 1% by mass, the specific polymer does not sufficiently adhere to the latex particles, and agglutination tends to occur during storage of the reagent for a latex agglutination reaction. If the content of the repeating unit (B) is 40% by mass or more, agglutination tends to occur during storage of the reagent for a latex agglutination reaction.

The content of the repeating unit (B) is preferably 2.5% by mass or more, and particularly preferably 5% by mass or more relative to all repeating units from a viewpoint that the specific polymer easily adheres to the particles. The content of the repeating unit (B) is preferably 38% by mass or less, more preferably 35% by mass or less, still more preferably 30% by mass or less, and particularly preferably 25% by mass or less relative to all repeating units from a viewpoint of suppressing agglutination during storage of the reagent for a latex agglutination reaction.

In particular, by setting the content of the repeating unit (B) to 25% by mass or less, even in a case where the reagent for a latex agglutination reaction is stored under a high temperature condition for a long period of time, the latex particles hardly agglutinate.

The specific polymer preferably contains one or more selected from the group consisting of a keto group, an ester bond, an amide bond, and an aromatic hydrocarbon group (for example, an aryl group such as a phenyl group or an arylene group such as a phenylene group) in the repeating unit (B). Note that the specific polymer may have the keto group or the like in a main chain or a side chain of the repeating unit (B), but preferably has the keto group or the like in the side chain of the repeating unit (B).

Examples of the repeating unit (B) include a repeating unit derived from a monomer having an unsaturated bond at a terminal thereof or a non-terminal thereof. Specific examples of the repeating unit include a repeating unit derived from a (meth)acrylamide-based monomer, a repeating unit derived from a (meth)acrylate-based monomer, and a repeating unit derived from a styrene-based monomer. As the repeating unit (B), these units may be used singly or in combination of two or more kinds thereof. Note that examples of the styrene-based monomer include styrene, 4-methylstyrene, 2,4-dimethylstyrene, 2,4,6-trimethylstyrene, 4-ethylstyrene, 4-isopropylstyrene, 4-tert-butylstyrene, and α-methyl styrene.

Among these units, the repeating unit (B) is preferably a (meth)acrylamide-based repeating unit, a (meth)acrylate-based repeating unit, or a styrene-based repeating unit, and more preferably a (meth)acrylamide-based repeating unit or a (meth)acrylate-based repeating unit.

The repeating unit (B) is preferably a hydrophobic repeating unit represented by the following formula (7) or (8), and more preferably a hydrophobic repeating unit derived from an alkyl (meth)acrylate or a hydrophobic repeating unit represented by formula (8) from a viewpoint of improving hydrophobicity and suppressing nonspecific adsorption.

Note that both a hydrophobic repeating unit represented by formula (7) and a hydrophobic repeating unit represented by formula (8) may be contained.

(7)

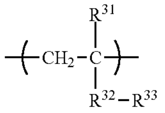

[In formula (7), $R^{31}$ represents a hydrogen atom or a methyl group, $R^{32}$ represents —O—, *—(C═O)—O—, *—(C═O)—NR$^{34}$—, *—NR$^{34}$—(C═O)— ($R^{34}$ represents a hydrogen atom or an organic group having 1 to 10 carbon atoms, and * represents a position bonded to a carbon atom to which $R^3$ in formula (7) is bonded), or a phenylene group, and $R^{33}$ represents a hydrocarbon group.]

(8)

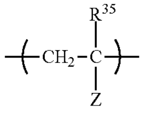

[In formula (8), $R^{35}$ represents a hydrogen atom or a methyl group, and

Z represents an organic group having a formyl group or a keto group.]

Each symbol in formula (7) will be described.

In formula (7), $R^{32}$ represents —O—, *—(C═O)—O—, *—(C═O)—NR$^{34}$—, *—NR$^{34}$—(C═O)—, or a phenylene group. Examples of such a phenylene group include a 1,2-phenylene group, a 1,3-phenylene group, and a 1,4-phenylene group.

Among $R^{32}$s, *—(C═O)—O—, *—(C═O)—NR$^{34}$—, and a phenylene group are preferable, *—(C═O)—O— and *—(C═O)—NR$^{34}$— are more preferable, and *—(C═O)—O— and *—(C═O)—NH— are particularly preferable from viewpoints, for example, of a desired effect of the present invention and availability.

$R^{33}$ represents a hydrocarbon group. The number of carbon atoms of the hydrocarbon group is preferably 1 to 30, more preferably 1 to 24, still more preferably 1 to 18, and particularly preferably 1 to 14.

The number of carbon atoms of the organic group represented by $R^{34}$ is 1 to 10, and preferably 1 to 6. Examples of the organic group include a hydrocarbon group.

Here, the hydrocarbon group in $R^{33}$ or $R^{34}$ is a concept including an aliphatic hydrocarbon group, an alicyclic hydrocarbon group, and an aromatic hydrocarbon group. The hydrocarbon group may be linear or branched and may contain a cyclic structure.

The aliphatic hydrocarbon group in the $R^{33}$ or $R^{34}$ may be linear or branched, and specific examples thereof include an alky group such as a methyl group, an ethyl group, an n-propyl group, an isopropyl group, an n-butyl group, an isobutyl group, a sec-butyl group, a tert-butyl group, a pentyl group, a hexyl group, a heptyl group, an octyl group, a nonyl group, or a decyl group.

The alicyclic hydrocarbon group is roughly classified into a monocyclic alicyclic hydrocarbon group and a bridged cyclic hydrocarbon group. Examples of the monocyclic alicyclic hydrocarbon group include a cycloalkyl group such as a cyclopropyl group or a cyclohexyl group. Examples of the bridged cyclic hydrocarbon group include an isobornyl group.

Examples of the aromatic hydrocarbon group include an aryl group such as a phenyl group.

Among these groups, $R^{33}$ is preferably an alkyl group. The number of carbon atoms of the alkyl group is preferably 1 to 30, more preferably 1 to 24, still more preferably 1 to 18, and particularly preferably 1 to 14 similarly to the above case.

A monomer constituting a repeating unit represented by formula (7) is preferably an alkyl (meth)acrylate. Specific examples of the alkyl (meth)acrylate include methyl (meth) acrylate, 2-ethylhexyl (meth)acrylate, lauryl (meth)acrylate, and stearyl (meth)acrylate. These monomers may be used singly or in combination of two or more kinds thereof.

Next, each symbol in formula (8) will be described.

In formula (8), $R^{35}$ represents a hydrogen atom or a methyl group and preferably represents a hydrogen atom.

Z represents an organic group having a formyl group or a keto group. The total number of carbon atoms of the organic group is preferably 4 or more, more preferably 4 to 13, still more preferably 5 to 11, and particularly preferably 6 to 9. The number of formyl groups or keto groups is not particularly limited as long as being one or more, and is preferably one.

Z preferably has an ester bond or an amide bond. The number of ester bonds or amide bonds is not particularly limited, and is preferably one.

Z is preferably an organic group having one formyl group or one keto group and having one ester bond or one amide bond, and more preferably a group represented by the following formula (9).

(9)

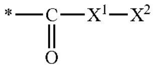

[In formula (9), $X^1$ represents —O— or —NH—, $X^2$ represents an organic group having a formyl group or a keto group and having 3 to 12 (preferably 4 to 10, more preferably 5 to 8) carbon atoms, and

* represents an atomic bond.]

$X^1$ is preferably —NH—.

$X^2$ is preferably a group represented by the following formula (10).

$$*{-}R^{36}{-}X^3 \qquad (10)$$

[In formula (10), $R^{36}$ represents a linear or branched alkanediyl group having 2 to 10 (preferably 3 to 8, more preferably 4 to 6) carbon atoms, $X^3$ represents a formyl group or —(C═O)—CH, and

* represents an atomic bond.]

Specific preferable examples of $X^2$ include a group represented by the following formula (11) or (12). Among these groups, a group represented by formula (11) is more preferable, and a group represented by formula (13) is particularly preferable.

(11)

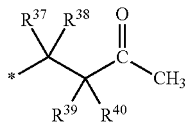

[In formula (11), $R^{37}$ to $R^{40}$ each independently represent a hydrogen atom, a methyl group, or an ethyl group, and

* represents an atomic bond.]

(12)

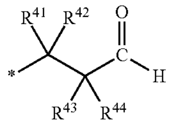

[In formula (12), $R^{41}$ to $R^{44}$ each independently represent a hydrogen atom, a methyl group, or an ethyl group, and

* represents an atomic bond.]

(13)

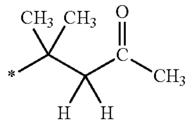

[In formula (13), * represents an atomic bond.]

Examples of a monomer constituting a repeating unit represented by formula (8) include diacetone (meth)acrylamide.

Note that the specific polymer only needs to contain one or more repeating units (A) and one or more repeating units (B). The specific polymer may contain a repeating unit other than the repeating units (A) and (B).

(Molecular Weight)

The specific polymer used in the present invention has a weight average molecular weight of 3,000 or more. If the weight average molecular weight is less than 3,000, the specific polymer hardly adheres to surfaces of the particles, and agglutination tends to occur during storage of the reagent for a latex agglutination reaction.

The weight average molecular weight (Mw) of the specific polymer is preferably 4,000 or more, more preferably 5,000 or more, still more preferably 6,000 or more, still more preferably 7,000 or more, still more preferably 8000 or more, still more preferably 9000 or more, still more preferably 10,000 or more, still more preferably 15,000 or more, still more preferably 20,000 or more, still more preferably 50,000 or more, still more preferably 70,000 or more, still more preferably 100,000 or more, still more preferably 125,000 or more, and particularly preferably 150,000 or more from viewpoints of adsorption force to surfaces of the particles and a prozone suppression effect. The weight average molecular weight (Mw) of the specific polymer is preferably one million or less, more preferably 300,000 or less, still more preferably 270,000 or less, further still more preferably 250,000 or less, and particularly preferably 225,000 or less from a viewpoint of, for example, maintaining sensitivity of an antibody antigen reaction in a ligand in a case where the ligand is immobilized to surfaces of the particles.

The number average molecular weight (Mn) of the specific polymer is preferably 500 to 100,000, more preferably 700 to 95,000, still more preferably 1,000 to 90,000, still more preferably 1,500 to 85,000, still more preferably 3,000 to 80,000, and particularly preferably 10,000 to 75,000.

A molecular weight distribution (Mw/Mn) is preferably 1 to 10, more preferably 1.5 to 8, still more preferably 1.8 to 7, and particularly preferably 2 to 6.

Note that the weight average molecular weight, the number average molecular weight, and the molecular weight distribution only need to be measured according to methods described below in Examples.

Note that the term “prozone” means a phenomenon that agglutination of the particles due to a reaction (for example, an antigen antibody reaction) between a ligand and a target substance (for example, an antigen) is suppressed and the concentration of the target substance cannot be measured accurately in a case where the target substance is in an excessive state.

(Other Physical Properties)

The specific polymer is preferably water-soluble. In addition to water, the specific polymer may be a polymer soluble in an organic solvent (for example, acetone, ethanol, or N-methylpyrrolidone).

In this case, herein, if the specific polymer is visually transparent in a case where the specific polymer is added to and mixed with water (25° C.) so as to have a polymer solid content of 0.5% by mass, the specific polymer is water-soluble.

If the specific polymer is visually transparent in a case where the specific polymer is added to and mixed with the organic solvent (25° C.) so as to have a polymer solid content of 0.5% by mass, the specific polymer is soluble in the organic solvent.

The specific polymer only needs to be a copolymer, and may be any one of a block copolymer, a random copolymer, an alternating copolymer, and a graft copolymer.

The specific polymer can be obtained, for example, by mixing monomers from which repeating units are derived and, if necessary, dissolving or dispersing the resulting mixture in a solvent such as water, acetonitrile, or Equamide B-100 (manufactured by Idemitsu Kosan Co., Ltd.), and adding a polymerization initiator thereto to perform radical polymerization.

The polymerization initiator is not particularly limited as long as being an ordinary radical polymerization initiator, and examples thereof include benzoyl peroxide, lauroyl peroxide, diisopropyl peroxydicarbonate, t-butyl peroxy-2-ethylhexanoate, t-butyl peroxypivalate, t-butylperoxy diisobutyrate, azobisisobutyronitrile, azobisisodimethylvaleronitrile, 2,2'-azobis(2-methylpropionamidine) dihydrochloride, a persulfate, and a persulfate-hydrogensulfite-based compound.

The use amount of the polymerization initiator is preferably 0.001 to 10 parts by mass, and more preferably 0.01 to 5 parts by mass relative to 100 parts by mass of the total of all monomers. The polymerization temperature is preferably 20 to 100° C., and the polymerization time is preferably 0.5 to 48 hours.

The content of the specific polymer in each of the additive and the surface treatment agent of the present invention is preferably 0.01 to 100% by mass, and more preferably 0.1 to 80% by mass.

Each of the additive and the surface treatment agent of the present invention may contain a solvent in addition to the specific polymer. Examples of the solvent include water; a lower alcohol such as ethanol, methanol, or isopropanol; a ketone such as acetone, methyl ethyl ketone, or methyl isobutyl ketone; an acetate such as ethyl acetate or butyl acetate; an amide such as dimethylformamide; and a sulfoxide such as dimethylsulfoxide.

As described in the following Examples, by adding the specific polymer to latex particles that have not been subjected to blocking treatment and by treating surfaces of the latex particles with the specific polymer, agglutination of the latex particles is suppressed in a case where the latex particles are stored while being contained in the reagent for a latex agglutination reaction, and storage stability of the latex particles is improved. In addition, an effect of reducing detection noise caused by agglutination of the latex particles due to nonspecific adsorption can be expected. Furthermore, there is a prozone suppression effect, for example.

Therefore, the specific polymer is useful as an additive to latex particles that have not been subjected to blocking treatment and a surface treatment agent for the latex particles, and can be used for a surface treatment method. In addition, the additive and the surface treatment agent of the present invention can be used, for example, as a blocking agent, a latex particle agglutination inhibitor, a latex particle storage stabilizer, or a detection noise reducing agent, and may also be used as a prozone inhibitor. The specific polymer can be expected to be used as a substitute for a biological substance that has been conventionally used as a blocking agent, such as albumin, casein, gelatin, or skim milk.

Note that the term "blocking" referred to herein means suppressing nonspecific adsorption to latex particles. Suppression of nonspecific adsorption to latex particles is a concept including reduction of detection noise caused by agglutination of the latex particles due to nonspecific adsorption to the latex particles.

<Surface-Modified Latex Particles>

The surface-modified latex particles of the present invention have a specific polymer on surfaces thereof.

The term "latex particles" referred to herein means latex particles used in a reagent for a latex agglutination reaction, and is a concept including both latex particles dispersed in a solvent and latex particles not in coexistence with a solvent. In the surface-modified latex particles of the present invention, the latex particles are preferably latex particles that have not been subjected to blocking treatment as a substance other than the specific polymer.

The term "surface-modified latex particles" means particles in which the specific polymer is in direct contact with a part or the whole of surfaces of the latex particles.

The average particle diameter of the latex particles is preferably 0.01 to 10 μm, and more preferably 0.05 to 1 μm. By setting the average particle diameter to 0.05 μm or more, an optical signal sensitizing effect is improved. By setting the average particle diameter to 10 μm or less, dispersion stability in a solvent is improved.

The average particle diameter of the latex particles means a volume average particle diameter before ligand immobilization and surface treatment, measured by laser diffraction/scattering particle diameter distribution measurement.

A ligand for a target substance is preferably immobilized to the latex particles. Examples of the ligand include an antibody and an antigen against a target substance.

The ligand may be immobilized to the latex particle by chemical bonding or physical adsorption but is preferably immobilized by chemical bonding. According to the present invention, a prozone can be suppressed in a case where the ligand and the latex particles are immobilized by chemical bonding.

Note that it is only required to prepare the latex particles and to immobilize the ligand according to a conventional method. For example, it is only required to perform the immobilization by a chemical bonding method by chemically modifying surfaces of the latex particles or introducing functional groups thereinto.

The latex particles are preferably obtained by using at least one compound selected from the group consisting of a polymerizable unsaturated aromatic compound, a polymerizable unsaturated carboxylic acid compound, a polymerizable unsaturated sulfonic acid compound or a salt thereof, a polymerizable carboxylate compound, a polymerizable unsaturated carboxylic acid amide compound, a polymerizable unsaturated nitrile compound, a halogenated vinyl compound, and a conjugated diene compound, and more preferably obtained by using at least one compound selected from the group consisting of a polymerizable unsaturated aromatic compound, a polymerizable unsaturated carboxylic acid compound, a polymerizable unsaturated sulfonic acid compound or a salt thereof, and a polymerizable carboxylate compound.

Specific examples of such a compound include a polymerizable unsaturated aromatic compound such as styrene, chlorostyrene, α-methylstyrene, divinylbenzene, vinyltoluene, vinylnaphthalene, divinylnaphthalene, α-naphthyl (meth)acrylate, or β-naphthyl (meth)acrylate; a polymerizable unsaturated carboxylic acid compound such as (meth) acrylic acid, itaconic acid, maleic acid, or fumaric acid; a polymerizable unsaturated sulfonic acid compound or a salt thereof, such as sodium styrene sulfonate; and a polymerizable carboxylate compound such as methyl (meth)acrylate, ethyl (meth)acrylate, n-butyl (meth)acrylate, 2-hydroxyethyl (meth)acrylate, glycidyl (meth)acrylate, ethyleneglycol-di-(meth)acrylate, or tribromophenyl (meth)acrylate. In addition, as the above compound, for example, (meth) acrylonitrile, (meth)acrolein, (meth)acrylamide, N-methylol (meth)acrylamide, methylenebis(meth)acrylamide, butadiene, isoprene, vinyl acetate, vinylpyridine, N-vinyl pyrrolidone, vinyl chloride, vinylidene chloride, or vinyl bromide may be used.

Among these compounds, in a case of immobilization by chemical bonding, a copolymer containing a repeating unit derived from a polymerizable unsaturated aromatic compound and a repeating unit derived from at least one selected from the group consisting of a polymerizable unsaturated carboxylic acid compound and a polymerizable unsaturated sulfonic acid compound or a salt thereof is preferable, and in particular, a copolymer formed of styrene and at least one selected from the group consisting of a polymerizable unsaturated carboxylic acid compound and a polymerizable unsaturated sulfonic acid compound or a salt thereof is more preferable.

Meanwhile, in a case of immobilization by physical adsorption, particles can also be produced only with polystyrene.

<Method for Producing Surface-Modified Latex Particles>

The method for producing surface-modified latex particles according to the present invention is characterized by including a contact step of bringing a specific polymer into contact with latex particles. In such a production method, the latex particles are preferably latex particles that have not been subjected to blocking treatment.

The contact is preferably performed in a liquid phase. Examples of a solvent used in this case include similar compounds to the solvents that can be blended with the additive and the surface treatment agent.

The term “contact” means direct contact between the specific polymer and the latex particle such that the specific polymer adheres to a part or the whole of surfaces of the latex particles. Specific examples of the contact include a method for dispersing the latex particles in a liquid phase containing the specific polymer, for example, using a shaker.

The contact time is usually 10 minutes to 10 hours. The contact temperature is not particularly limited but is usually 10 to 60° C.

Note that the method for producing surface-modified latex particles according to the present invention may include a separation step of separating a remaining specific polymer, for example, by centrifugation after the contact step.

<Reagent for Latex Agglutination Reaction>

The reagent for a latex agglutination reaction of the present invention includes the surface-modified latex particle of the present invention or surface-modified latex particles obtained by the method for producing surface-modified latex particles according to the present invention.

In the reagent for a latex agglutination reaction of the present invention, the content of the surface-modified latex particles is preferably 0.1 to 3% by mass, more preferably 0.1 to 1% by mass, and particularly preferably 0.1 to 0.6% by mass.

In addition to the surface-modified latex particles, the reagent for a latex agglutination reaction of the present invention may contain a water-soluble polymer and a solvent. Examples of the water-soluble polymer include polyethylene glycol, a polyhydric alcohol, polyvinyl pyrrolidone, carboxymethyl cellulose, methyl cellulose, ethyl cellulose, saccharose, dextran, pullulan, polyamino acid, alginic acid, an aminoethanesulfonic acid derivative, an aminopropane sulfonic acid derivative, bovine serum albumin (BSA), casein, a block ace, gum arabic, a protein degradation product, an amino acid, a peptide, and a polypeptide. Examples of the solvent include various buffers such as a phosphate buffer a glycine buffer, a Good’s buffer, a Tris buffer, and an ammonia buffer in addition to a solvent that can be blended with the surface treatment agent.

Furthermore, the reagent for a latex agglutination reaction of the present invention may contain, for example, a salt, a surfactant, or a preservative, if necessary.

The reagent for a latex agglutination reaction of the present invention is useful for detecting a target substance in a specimen by a latex agglutination method.

<Kit>

The kit to be used for detecting a target substance in a specimen by a latex agglutination method according to the present invention is characterized by including the reagent for a latex agglutination reaction of the present invention.

The kit of the present invention preferably further includes a reaction buffer (also referred to as a first reagent) in addition to the reagent for a latex agglutination reaction of the present invention (also referred to as a second reagent).

The first reagent may contain the water-soluble polymer. In addition, the first reagent may contain a solvent and a sensitizer for latex agglutination measurement. Examples of the solvent include an aqueous medium. Examples of the aqueous medium include the various buffers.

Examples of the sensitizer for latex agglutination measurement include polyvinyl alcohol and polyvinyl pyrrolidone.

In addition to the first reagent and the second reagent, the kit of the present invention may include, for example, a positive control, a negative control, and a serum diluted solution. A medium for the positive control and the negative control may be a solvent such as the above aqueous media in addition to serum and physiological saline not containing a measurable target substance.

The kit of the present invention can be used for detecting a target substance in a similar manner to a general kit to be used for detecting a target substance in a specimen by a latex agglutination method. The concentration of a target substance can also be measured according to a conventional method.

<Method for Detecting Target Substance>

The method for detecting a target substance according to the present invention is characterized by including a mixing step of mixing the reagent for a latex agglutination reaction according to the present invention with a specimen, and a detection step of optically detecting an agglutination reaction generated in the mixing step.

The target substance means a detection target that may usually cause an immune reaction, such as an antigen, a virus, a pathogen, an antibody, or an autoantibody.

Examples of the target substance include a receptor, an enzyme, a blood protein (for example, a carcinoembryonic protein), an infectious disease-related antigen (for example, an antigen such as hepatitis B virus, hepatitis C virus, syphilis pathogen, human immunodeficiency virus, or pathogenic *Escherichia coli*), and antibodies against these antigens. The antibody includes, for example, a fragment of the antibody as long as having a bonding property to a specific antigen.

(Mixing Step)

The mixing step is a step of mixing the reagent for a latex agglutination reaction of the present invention with a specimen.

Examples of the specimen include various biological liquid samples such as serum, plasma, urine, or saliva, and a product obtained by pulverizing a specimen such as feces or food. As a measurement sample, a specimen diluted solution obtained by diluting a specimen, for example, with a protein such as albumin or globulin, a pH buffer, an amino acid, or a surfactant may be used.

The mixing temperature in the mixing step is usually in a range of 4 to 50° C., preferably in a range of 15 to 40° C., and more preferably in a range of 30 to 40° C.

The mixing time is usually 60 minutes or less. The pH of the mixed solution is usually in a range of 5 to 10. The pH of the mixed solution is more preferably in a range of 6 to 9 from a viewpoint of further improving stability of a complex of an antibody and an antigen.

(Detection Step)

The detection step optically detects an agglutination reaction generated in the mixing step. Due to this step, a target substance in a specimen can be detected, and the concentration of the target substance can be also measured.

It is only required to perform the detection step using a known apparatus that can automatically track the degree of particle agglutination. Examples of such an apparatus include an optical device capable of detecting, for example, scattered light intensity, transmitted light intensity, and absorbance.

As a method for optically detecting the degree of particle agglutination, a known method can be used, and examples thereof include (1) a turbidimetric method for regarding formation of agglutination as an increase in turbidity, (2) a method for regarding formation of agglutination as a change in particle size distribution or average particle size, and (3) an integrating sphere turbidity method for measuring a change in forward scattered light due to formation of agglutination and comparing a ratio with transmitted light intensity.

The above measuring methods can use, for example, a rate assay of obtaining at least two measurement values at different time points and determining an increase in measurement value between these time points, that is, the degree of agglutination based on the increasing rate, or an end point assay of obtaining one measurement value at a point considered to be an end point of a reaction and determining the degree of agglutination based on this measurement value. However, the rate assay by the turbidimetric method is preferable from viewpoints of convenience and rapidity of measurement.

Examples of an automated clinical test machine suitable for immunolatex agglutination reaction measurement using the method for detecting a target substance according to the present invention include a commercially available automatic analyzer such as Hitachi 7070, 7150, 7170, 7180, LPIA-A700, or 5500.

The method for detecting a target substance according to the present invention makes a difference between a change in absorbance in a low value region and a background clear in measurement of turbidity or absorbance. This can enhance detection sensitivity of a target substance. In addition, occurrence of a prozone can be suppressed.

EXAMPLES

Hereinafter, the present invention will be described in detail based on Examples, but the present invention is not limited to the Examples.

Measurement conditions of molecular weight in Examples are as follows.

The weight average molecular weight (Mw) and the number average molecular weight (Mn) were measured using a TSK gel α-M column manufactured by Tosoh Corporation under analysis conditions of flow rate: 0.5 ml/min, elution solvent: NMP solvent ($H_3PO_4$: 0.016 M, LiBr: 0.030 M), and column temperature: 40° C. by gel permeation chromatography (GPC) with polystyrene as standard.

Synthesis Example 1

A monomer composition containing 2.0 g of 4-acryloyl morpholine (hereinafter referred to as ACMO (manufactured by Kohjin Film & Chemicals Co., Ltd.)), 2.5 g of methoxypolyethylene glycol methacrylate having an average addition molar number of ethylene oxide of 9 (hereinafter referred to as M90G (manufactured by Shin-Nakamura Chemical Co., Ltd.)), and 0.5 g of diacetone acrylamide (hereinafter referred to as DAAM) was mixed with 40.05 g of water, and the resulting mixture was put in a flask and stirred with a stirrer. While nitrogen was blown into the mixture, the temperature of the mixture was raised to 60° C., and 5 g of a 10% by mass aqueous solution of 2,2'-azobis (2-methylpropionamidine) dihydrochloride as a polymerization initiator and 0.01 g of α-thio glycerol as a chain transfer agent were added thereto. The resulting mixture was polymerized for three hours and then cooled to room temperature. The obtained copolymer is referred to as a copolymer (P1).

The weight average molecular weight (Mw) of the obtained copolymer (P1) by GPC was 107,400 and Mw/Mn thereof was 4.01.

Synthesis Example 2

A copolymer was synthesized in a similar manner to Synthesis Example 1 except that the monomer composition was changed to a monomer composition containing 2.0 g of ACMO, 2.25 g of M90G, 0.25 g of N-methacryloyloxyethyl-N,N-dimethylammonium-α-N-methylcarboxybetaine (hereinafter referred to as GLBT (manufactured by Osaka Organic Chemical Industry Ltd.)), and 0.5 g of methyl methacrylate (hereinafter referred to as MMA). The obtained copolymer is referred to as a copolymer (P2).

Synthesis Example 3

A copolymer was synthesized in a similar manner to Synthesis Example 1 except that the monomer composition was changed to a monomer composition containing 1.5 g of ACMO, 0.25 g of N,N-dimethylacrylamide (hereinafter referred to as DMAA), 1.0 g of M90G, 1.25 g of methoxypolyethylene glycol methacrylate having an average addition molar number of ethylene oxide of 23 (hereinafter referred to as M230G (manufactured by Shin-Nakamura Chemical Co., Ltd.)), 0.75 g of GLBT, and 0.25 g of MMA. The obtained copolymer is referred to as a copolymer (P3).

Synthesis Example 4

A copolymer was synthesized in a similar manner to Synthesis Example 1 except that the monomer composition was changed to a monomer composition containing 1.0 g of ACMO, 0.5 g of DMAA, 1.25 g of M90G, 1.25 g of M230G, and 1.0 g of DAAM. The obtained copolymer is referred to as a copolymer (P4).

Synthesis Example 5

A copolymer was synthesized in a similar manner to Synthesis Example 1 except that the monomer composition was changed to a monomer composition containing 2.0 g of ACMO, 2.5 g of DMAA, and 0.5 g of DAAM. The obtained copolymer is referred to as a copolymer (P5).

Synthesis Example 6

A copolymer was synthesized in a similar manner to Synthesis Example 1 except that the monomer composition was changed to a monomer composition containing 1.0 g of ACMO, 1.75 g of DMAA, 1.0 g of M230G, 0.25 g of GLBT, and 1.0 g of MMA. The obtained copolymer is referred to as a copolymer (P6).

Synthesis Example 7

A copolymer was synthesized in a similar manner to Synthesis Example 1 except that the monomer composition was changed to a monomer composition containing 2.0 g of DMAA, 1.5 g of M90G, and 1.5 g of DAAM. The obtained copolymer is referred to as a copolymer (P7).

Synthesis Example 8

A copolymer was synthesized in a similar manner to Synthesis Example 1 except that the monomer composition was changed to a monomer composition containing 3.5 g of DMAA and 1.5 g of DAAM. The obtained copolymer is referred to as a copolymer (P8).

Synthesis Example 9

A copolymer was synthesized in a similar manner to Synthesis Example 1 except that the monomer composition was changed to a monomer composition containing 1.0 g of ACMO, 3.0 g of DMAA, and 1.0 g of MMA. The obtained copolymer is referred to as a copolymer (P9).

Synthesis Example 10

A copolymer was synthesized in a similar manner to Synthesis Example 1 except that the monomer composition was changed to a monomer composition containing 2.0 g of ACMO, 2.75 g of M90G, and 0.25 g of MMA. The obtained copolymer is referred to as a copolymer (P 10).

Synthesis Example 11

A copolymer was synthesized in a similar manner to Synthesis Example 1 except that the monomer composition was changed to a monomer composition containing 1.0 g of ACMO, 2.25 g of M 230G, and 1.75 g of DAAM. The obtained copolymer is referred to as a copolymer (P11).

Comparative Synthesis Example 1

A copolymer was synthesized in a similar manner to Synthesis Example 1 except that the monomer composition was changed to a monomer composition containing 2.0 g of ACMO, 2.5 g of M90G, and 0.5 g of DAAM. The obtained copolymer is referred to as a copolymer (P12).

Comparative Synthesis Example 2

A copolymer was synthesized in a similar manner to Synthesis Example 1 except that the monomer composition was changed to a monomer composition containing 0.5 g of ACMO, 2.25 g of M90G, 0.25 g of GLBT, and 2.0 g of MMA. The obtained copolymer is referred to as a copolymer (P13).

Reference Example

A homopolymer formed of a repeating unit derived from ACMO, a homopolymer formed of a repeating unit derived from DMAA, a homopolymer formed of a repeating unit derived from M90G, a homopolymer formed of a repeating unit derived from M230G, and a homopolymer formed of a repeating unit derived from GLBT (each having a number average molecular weight of about 10,000) were each synthesized, and 1 g of each of the homopolymers was added to 100 g of pure water and dissolved therein at room temperature (25° C.)

A homopolymer formed of a repeating unit derived from DAAM and a homopolymer formed of a repeating unit derived from MMA (each having a number average molecular weight of about 10,000) were each synthesized, and 1 g of each of the homopolymers was added to 100 g of pure water and was not completely dissolved therein at room temperature (25° C.)

Preparation Example 1: Preparation of R1 Buffer 1.19 g of HEPES and 1 g of sodium chloride were dissolved in 70 g of distilled water. The obtained aqueous solution was mixed with 4.5 g of a 2% by mass aqueous solution of sodium azide, and then the pH was adjusted to about 7.5 to obtain 100 g of an aqueous solution in total.

The obtained aqueous solution is referred to as a R1 buffer. Note that the concentration of sodium azide is 0.09% by mass in the R1 buffer.

Preparation Example 2: Preparation of R2 Buffer (1)

1.19 g of HEPES and 1 g of sodium chloride were dissolved in 70 g of distilled water. The obtained aqueous solution was mixed with 4.5 g of a 2% by mass aqueous solution of sodium azide, and then the pH was adjusted to about 7.5 to obtain 100 g of an aqueous solution in total.

The obtained aqueous solution is referred to as a R2 buffer (1). Note that the concentration of sodium azide is 0.09% by mass in the R2 buffer (1).

Preparation Example 3: Preparation of R2 Buffer (2)

1.19 g of HEPES and 1 g of sodium chloride were dissolved in 70 g of distilled water. The obtained aqueous solution was mixed with 4.5 g of a 2% by mass aqueous solution of sodium azide, and a 10% by mass aqueous solution of the copolymer (P5) was added thereto. Thereafter, the pH was adjusted to about 7.5 to obtain 100 g of an aqueous solution in total.

The obtained aqueous solution is referred to as a R2 buffer (2). Note that the concentration of the copolymer (P5) is 2% by mass and the concentration of sodium azide is 0.09% by mass in the R2 buffer (2).

Example 1

(Immobilization of Antibody to Latex Particles)

1.4 mL of a 5.3% by mass aqueous dispersion of immunodiagnostic latex particles (having a carboxy group on surfaces thereof, average particle diameter: 0.082 μm (IMMUTEX P0011 manufactured by JSR Life Sciences Corporation)), 0.75 mL of a 0.5 M HEPES buffer, and 4.9 mL of distilled water were mixed. To this particle dispersion, 0.46 mL of a 16.3 mg/mL aqueous solution of an anti-CRP antibody (rabbit) was added, and the resulting mixture was stirred at room temperature for one hour. Subsequently, 0.15 mL of a 1% by mass aqueous solution of 1-ethyl-3-(3-dimethylaminopropyl) carbodiimide hydrochloride (hereinafter referred to as WSC (manufactured by Dojindo Laboratories)) was added thereto and stirred at room temperature for one hour. Subsequently, 0.51 mL of this particle dispersion was transferred to a centrifuge tube and centrifuged at 15,000 rpm for 10 minutes to remove a supernatant containing an unreacted anti-CRP antibody and WSC, and antibody-immobilized latex particles were collected as a precipitate.

(Surface Treatment of Latex Particles with Surface Treatment Agent (Addition of Additive to Latex Particles that have not been Subjected to Blocking Treatment))

Subsequently, 1 mL of a 0.5% by mass aqueous solution of the copolymer (P1) was prepared, and added to the antibody-immobilized latex particles. The particles were dispersed with an aluminum block shaker for one hour. Subsequently, the obtained particle dispersion was centrifuged at 15,000 rpm for 10 minutes to remove a supernatant containing the remaining copolymer (P1). In this way, a dispersion (surface-modified latex particle dispersion) of the antibody-immobilized latex particles surface-treated with the copolymer (P1) was obtained.

(Preparation of Reagent for Latex Agglutination Reaction)

Subsequently, 5 mL of the R2 buffer (1) obtained in Preparation Example 2 was added to the dispersion of the surface-treated antibody-immobilized latex particles to obtain a reagent 1 for a latex agglutination reaction.

Examples 2 to 4

Reagents 2 to 4 for a latex agglutination reaction were obtained in a similar manner to Example 1 except that the copolymer (P1) was changed to the copolymer (P2), the copolymer (P3), and the copolymer (P4), respectively.

Examples 5 and 6

Reagents 5 and 6 for a latex agglutination reaction were obtained in a similar manner to Example 1 except that the immunodiagnostic latex particles having a carboxy group on surfaces thereof were changed to immunodiagnostic latex particles having no carboxy group on surfaces thereof (average particle diameter: 0.121 μm, IMMUTEX P2117 manufactured by JSR Life Sciences Corporation) and the copolymer (P1) was changed to the copolymer (P5) and the copolymer (P6), respectively.

Examples 7 to 11

Reagents 7 to 11 for a latex agglutination reaction were obtained in a similar manner to Example 1 except that the copolymer (P1) was changed to the copolymer (P7), the copolymer (P8), the copolymer (P9), the copolymer (P10), and the copolymer (P11), respectively.

Comparative Example 1

A reagent 12 for a latex agglutination reaction was obtained in a similar manner to Example 1 except that the copolymer (P1) was changed to the copolymer (P12).

Comparative Example 2

A reagent 13 for a latex agglutination reaction was obtained in a similar manner to Example 1 except that the copolymer (P1) was changed to the copolymer (P13).

Comparative Example 3

A reagent 14 for a latex agglutination reaction was obtained in a similar manner to Example 1 except that the copolymer (P1) was changed to bovine serum albumin (BSA).

Comparative Example 4

A reagent 15 for a latex agglutination reaction was obtained in a similar manner to Example 1 except that the immunodiagnostic latex particles having a carboxy group on surfaces thereof were changed to immunodiagnostic latex particles having no carboxy group on surfaces thereof (average particle diameter: 0.121 μm, IMMUTEX P2117 manufactured by JSR Life Sciences Corporation) and the copolymer (P1) was changed to bovine serum albumin (BSA).

Comparative Example 5

As a comparative example in which the copolymer (P5) was used not as a surface treatment agent (additive to latex particles that have not been subjected to blocking treatment) but as a sensitizer, a reagent for a latex agglutination reaction obtained by adding antibody-immobilized latex particles previously surface-treated with bovine serum albumin and the copolymer (P5) to a dispersion medium was prepared.

That is, 1.4 mL of a 5.3% by mass aqueous dispersion of immunodiagnostic latex particles (average particle size: 0.121 μm, IMMUTEX P2117 manufactured by JSR Life Sciences Corporation) having no carboxy group on surfaces thereof, 0.75 mL of a 0.5 M HEPES buffer, and 4.9 mL of distilled water were mixed. To this particle dispersion, 0.46 mL of a 16.3 mg/mL aqueous solution of an anti-CRP antibody (rabbit) was added, and the resulting mixture was stirred at room temperature for one hour. Subsequently, this particle dispersion was transferred to a centrifuge tube and centrifuged at 15,000 rpm for 10 minutes to remove a supernatant containing an unreacted anti-CRP antibody, and antibody-immobilized latex particles were collected as a precipitate.

Subsequently, 1 mL of a 0.5% by mass aqueous solution of bovine serum albumin (BSA) was prepared, and added to the antibody-immobilized latex particles. The particles were dispersed with an aluminum block shaker for one hour. Subsequently, the obtained particle dispersion was centrifuged at 15,000 rpm for 10 minutes to remove a supernatant containing the remaining bovine serum albumin (BSA). In this way, a dispersion of the antibody-immobilized latex particles surface-treated with bovine serum albumin (BSA) was obtained.

Subsequently, 5 mL of the R2 buffer (2) obtained in Preparation Example 3 was added to the dispersion of the surface-treated antibody-immobilized latex particles to obtain a reagent 16 for a latex agglutination reaction.

Comparative Example 6

A reagent 17 for latex agglutination reaction was obtained in a similar manner to Example 1 except that the 0.5% by mass aqueous solution of the copolymer (P1) was changed to distilled water.

Comparative Example 7

A reagent 18 for a latex agglutination reaction was obtained in a similar manner to Example 1 except that the immunodiagnostic latex particles having a carboxy group on surfaces thereof were changed to immunodiagnostic latex particles having no carboxy group on surfaces thereof (average particle diameter: 0.121 μm, IMMUTEX P2117 manufactured by JSR Life Sciences Corporation) and the 0.5% by mass aqueous solution of the copolymer (P1) was changed to distilled water.

Test Example 1: Stability Evaluation Test

The reagent for a latex agglutination reaction prepared in each of Examples and Comparative Examples was allowed to stand at 4° C. overnight, and presence or absence of precipitation was visually observed. Evaluation was performed in accordance with the following criteria. The reagent for a latex agglutination reaction prepared in each of Examples and Comparative Examples was allowed to stand at 4° C. overnight and further allowed to stand at 37° C. for one week, and the presence or absence of precipitation was visually observed. Evaluation was performed according to the following criteria. These results are illustrated in Tables 1 and 2.

(Stability Evaluation Criteria)

AA: Precipitation of particles was not observed
A: Precipitation of particles was hardly observed
B: Precipitation of particles was slightly observed
C: Precipitation of particles was clearly observed

TABLE 1

| | | | Examples | | | | | | | | | | |
|---|---|---|---|---|---|---|---|---|---|---|---|---|---|
| | | | 1 | 2 | 3 | 4 | 5 | 6 | 7 | 8 | 9 | 10 | 11 |
| Surface treatment agent (additive) | | | P1 | P2 | P3 | P4 | P5 | P6 | P7 | P8 | P9 | P10 | P11 |
| Repeating unit (Parts by mass) | (A) | ACMO | 40 | 40 | 30 | 20 | 40 | 20 | 0 | 0 | 20 | 40 | 20 |
| | | DMAA | 0 | 0 | 5 | 10 | 50 | 35 | 40 | 70 | 60 | 0 | 0 |
| | | M90G | 50 | 45 | 20 | 25 | 0 | 0 | 30 | 0 | 0 | 55 | 0 |
| | | M230G | 0 | 0 | 25 | 25 | 0 | 20 | 0 | 0 | 0 | 0 | 45 |
| | | GLBT | 0 | 5 | 15 | 0 | 0 | 5 | 0 | 0 | 0 | 0 | 0 |
| | (B) | DAAM | 10 | 0 | 0 | 20 | 10 | 0 | 30 | 30 | 0 | 0 | 35 |
| | | MMA | 0 | 10 | 5 | 0 | 0 | 20 | 0 | 0 | 20 | 5 | 0 |
| Weight average molecular weight ($\times 10^4$) | | | 10.74 | 0.61 | 20.26 | 2.05 | 7.11 | 1.53 | 0.59 | 10.31 | 0.71 | 0.92 | 0.85 |
| Mw/Mn | | | 4.01 | 3.97 | 2.84 | 3.05 | 4.66 | 3.11 | 4.74 | 4.29 | 4.25 | 3.51 | 3.33 |
| Immobilization method between particles and antibody | | | Chemical bonding | Chemical bonding | Chemical bonding | Chemical bonding | Physical adsorption | Physical adsorption | Chemical bonding | Chemical bonding | Chemical bonding | Chemical bonding | Chemical bonding |
| R2 buffer | | | (1) | (1) | (1) | (1) | (1) | (1) | (1) | (1) | (1) | (1) | (1) |
| Stability | Allowed to stand at 4° C. overnight | | AA | AA | AA | AA | AA | AA | AA | AA | AA | AA | AA |
| | Allowed to stand at 4° C. overnight and further allowed to stand at 37° C. for one week | | AA | AA | AA | AA | AA | AA | B | B | AA | AA | A |

TABLE 2

| | | | Comparative Example | | | | | | |
|---|---|---|---|---|---|---|---|---|---|
| | | | 1 | 2 | 3 | 4 | 5 | 6 | 7 |
| Surface treatment agent (additive) | | | P12 | P13 | BSA | BSA | BSA | None | None |
| Repeating unit (Parts by mass) | (A) | ACMO | 40 | 10 | — | — | — | — | — |
| | | DMAA | 0 | 0 | | | | | |
| | | M90G | 50 | 45 | | | | | |
| | | M230G | 0 | 0 | | | | | |
| | | GLBT | 0 | 5 | | | | | |
| | (B) | DAAM | 10 | 0 | | | | | |
| | | MMA | 0 | 40 | | | | | |
| Weight average molecular weight ($\times 10^4$) | | | 0.23 | 0.59 | 6.6 | 6.6 | 6.6 | — | — |
| Mw/Mn | | | 2.99 | 3.56 | — | — | — | — | — |
| Immobilization method between particles and antibody | | | Chemical bonding | Chemical bonding | Chemical bonding | Physical absorption | Physical absorption | Chemical bonding | Physical absorption |
| R2 buffer | | | (1) | (1) | (1) | (1) | (2) | (1) | (1) |
| Stability | Allowed to stand at 4° C. overnight | | C | C | C | C | C | C | C |
| | Allowed to stand at 4° C. overnight and further allowed to stand at 37° C. for one week | | C | C | C | C | C | C | C |

As illustrated in Table 1, in a case where surfaces of the antibody-immobilized latex particles were treated with the copolymers (P1) to (P11) (Examples 1 to 11), occurrence of precipitation of the particles was suppressed. This indicates that by adding the specific polymer of the present invention to latex particles that have not been subjected to blocking treatment, that is, by treating surfaces of the latex particles with the specific polymer of the present invention, agglutination of the latex particles is suppressed during storage of the reagent for a latex agglutination reaction.

As illustrated in Table 2, in a case where surfaces of antibody-immobilized latex particles were treated with the copolymer (P12) having a weight average molecular weight of less than 3,000 (Comparative Example 1), in a case where surfaces of antibody-immobilized latex particles were treated with the copolymer (P13) having the content of the repeating unit (A) of 60% by mass and the content of the repeating unit (B) of 40% by mass (Comparative Example 2), and in a case where surfaces of antibody-immobilized latex particles were treated with BSA (Comparative Examples 3 and 4), precipitation of the particles was clearly observed.

In addition, in a case where the antibody-immobilized latex particles and the copolymer (P5) were added to a dispersion medium (Comparative Example 5), precipitation of the particles was clearly observed. The antibody-immobilized latex particles used in Comparative Example 5 have already been surface-treated with BSA, and therefore the copolymer (P5) does not treat surfaces of the antibody-immobilized latex particles in the reagent. This indicates the following. That is, precipitation of the particles is not suppressed only by coexistence of the specific polymer of the present invention in a reagent like a sensitizer. In order to suppress the precipitation of the particles, it is necessary to add the specific polymer of the present invention to latex particles that have not been subjected to blocking treatment, that is, to treat surfaces of the latex particles with the specific polymer of the invention.

Test Example 2: Antigen Antibody Reactivity Evaluation Test

To a measurement cell, 3 μL of a physiological saline diluted solution of a target substance (CRP antigen) or a physiological saline thereof as a specimen and 100 μL of the R1 buffer obtained in Preparation Example 1 as a first reagent were added and stirred. Subsequently, 100 μL of the reagent for a latex agglutination reaction prepared in Example 1 as a second reagent was added to the measurement cell and stirred. Thereafter, using a Hitachi 7180 automatic analyzer, immunolatex agglutination measurement was performed under conditions of a main wavelength: 570 nm, a sub wavelength: 800 nm, and a measurement temperature: 37° C., and reactivity of an antigen-antibody reaction was checked. Note that tests were performed by setting the concentrations of the target substance in the physiological saline diluted solution to 0 mg/dL, 0.05 mg/dL, 0.1 mg/dL, 0.25 mg/dL, 0.5 mg/dL, 1 mg/dL, 2 mg/dL, and 4 mg/dL, respectively.

In addition, reactivity of the antigen-antibody reaction was checked in a similar manner to the above using the reagents for a latex agglutination reaction in Examples 3 and 4 and Comparative Example 3 as the second reagent.

FIG. 1 illustrates results of Test Example 2. As illustrated in FIG. 1, in a case where surfaces of the antibody-immobilized latex particles were treated with the copolymers (P1), (P3), and (P4) (Examples 1, 3, and 4), a prozone suppression effect was obtained.

The invention claimed is:

1. An additive for adding to latex particles, the additive comprises a polymer comprising:

from more than 60% by mass to 99% by mass of hydrophilic repeating units (A) relative to all repeating units, and from 1% by mass to less than 40% by mass of hydrophobic repeating units (B) relative to all repeating units, wherein the polymer has a weight average molecular weight of at least 3,000, and wherein the hydrophilic repeating units comprise:

a hydrophilic repeating unit of the following formula (6):

(6)

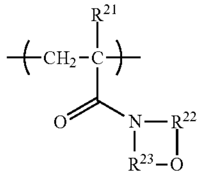

wherein $R^{21}$ represents a hydrogen atom or a methyl group, and $R^{22}$ and $R^{23}$ each independently represent an alkanediyl group comprising 1 to 3 carbon atoms, and a hydrophilic repeating unit of the following formula (2):

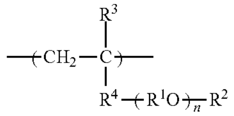

wherein $R^1$ represents an alkanediyl group comprising 2 to 4 carbon atoms, and n represents 2 to 100 as an average value, $R^2$ represents a hydrogen atom or an alkyl group comprising 1 to 4 carbon atoms, $R^3$ represents a hydrogen atom or a methyl group, $R^4$ represents —O—, *—(C═O)—O—, *—$NR^5$—(C═O), wherein $R^5$ represents a hydrogen atom or an organic group comprising 1 to 10 carbon atoms, and * represents a position bonded to a carbon atom to which $R^3$ in the formula (2) is bonded, or a phenylene group, wherein the hydrophobic repeating units comprise a hydrophobic repeating unit represented by the following formula (7) and a hydrophobic repeating unit represented by the following formula (8), (7)

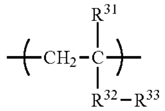

wherein $R^{31}$ represents a methyl group, $R^{32}$ represents —O—, *—(C═O)—O—, *—(C═O)—$NR^{34}$—, *—$NR^{34}$—(C═O)—, $R^{34}$ represents a hydrogen atom or an organic group having 1 to 10 carbon atoms, and * represents a position bonded to a carbon atom to which $R^{31}$ in formula (7) is bonded, or a phenylene group, and $R^{33}$ represents a hydrocarbon group, (8)

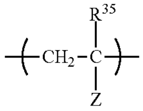

wherein $R^{35}$ represents a hydrogen atom or a methyl group, and

Z represents an organic group having a formyl group or a keto group.

2. A surface treatment agent for surface treatment of latex particles, the surface treatment agent comprises a polymer comprising:

from more than 60% by mass to 99% by mass of hydrophilic repeating units (A) relative to all repeating units, and from 1% by mass to less than 40% by mass of hydrophobic repeating units (B) relative to all repeating units, wherein the polymer has a weight average molecular weight of at least 3,000, and wherein the hydrophilic repeating units comprise:

a hydrophilic repeating unit of the following formula (6):

(6)

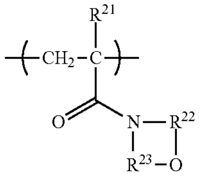

wherein $R^{21}$ represents a hydrogen atom or a methyl group, and $R^{22}$ and $R^{23}$ each independently represent an alkanediyl group comprising 1 to 3 carbon atoms, and a hydrophilic repeating unit of the following formula (2):

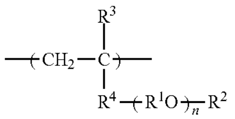

wherein $R^1$ represents an alkanediyl group comprising 2 to 4 carbon atoms, and n represents 2 to 100 as an average value, $R^2$ represents a hydrogen atom or an alkyl group comprising 1 to 4 carbon atoms, $R^3$ represents a hydrogen atom or a methyl group, $R^4$ represents —O—, *—(C═O)—O—, *—NR$^5$—(C═O), wherein $R^5$ represents a hydrogen atom or an organic group comprising 1 to 10 carbon atoms, and * represents a position bonded to a carbon atom to which $R^3$ in the formula (2) is bonded, or a phenylene group, wherein the hydrophobic repeating unit comprises a hydrophobic repeating unit represented by the following formula (7) and a hydrophobic repeating unit represented by the following formula (8), (7)

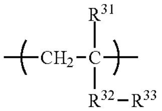

wherein $R^{31}$ represents a methyl group, $R^{32}$ represents —O—, *—(C═O)—O—, *—(C═O)—NR$^{34}$—, *—NR$^{34}$—(C—O)—, $R^{34}$ represents a hydrogen atom or an organic group having 1 to 10 carbon atoms, and * represents a position bonded to a carbon atom to which $R^{31}$ in formula (7) is bonded, or a phenylene group, and $R^{33}$ represents a hydrocarbon group, (8)

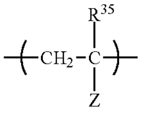

wherein $R^{35}$ represents a hydrogen atom or a methyl group, and

Z represents an organic group having a formyl group or a keto group.

3. The agent of claim 2, wherein the polymer has a weight average molecular weight of 3,000 to 1,000,000.

4. The agent of claim 2, wherein the polymer is water-soluble.

5. The agent of claim 1, wherein the polymer has a weight average molecular weight of from 3,000 to 300,000.

6. The agent of claim 2, wherein the polymer has a weight average molecular weight of from 3,000 to 300,000.

7. The agent of claim 1, wherein the polymer has a weight average molecular weight of 3,000 to 1,000,000.

* * * * *